US011898191B2

(12) United States Patent
González-Macia et al.

(10) Patent No.: US 11,898,191 B2
(45) Date of Patent: Feb. 13, 2024

(54) ENZYMATIC ELECTROCHEMICAL METHOD FOR THE QUANTIFICATION OF ANALYTES IN BIOLOGICAL FLUID SAMPLES

(71) Applicant: Biolan Health, S.L., Derio (ES)

(72) Inventors: Laura González-Macia, Derio (ES); Maitane Urien Berrio, Derio (ES); Roberto González Rioja, Derio (ES); Arrate Jaureguibeitia Cayrols, Derio (ES); Israel Sánchez Moreno, Derio (ES); Carmen Hermida Díaz, Derio (ES)

(73) Assignee: BIOLAN HEALTH, S.L., Derio (ES)

( * ) Notice: Subject to any disclaimer, the term of this patent is extended or adjusted under 35 U.S.C. 154(b) by 634 days.

(21) Appl. No.: 17/126,971

(22) Filed: Dec. 18, 2020

(65) Prior Publication Data

US 2021/0102232 A1 Apr. 8, 2021

Related U.S. Application Data

(63) Continuation-in-part of application No. PCT/EP2019/065994, filed on Jun. 18, 2019.

(30) Foreign Application Priority Data

Jun. 21, 2018 (EP) .................................... 18382459

(51) Int. Cl.
*C12Q 1/00* (2006.01)
*C12N 9/06* (2006.01)

(52) U.S. Cl.
CPC .......... *C12Q 1/005* (2013.01); *C12N 9/0016* (2013.01)

(58) Field of Classification Search
None
See application file for complete search history.

(56) References Cited

U.S. PATENT DOCUMENTS

| 6,736,957 | B1 | 5/2004 | Forrow |
| 2009/0018424 | A1 | 1/2009 | Kamath |
| 2010/0270175 | A1 | 10/2010 | Pei |

OTHER PUBLICATIONS

J.-K. Park, et al., "Determination of breath alcohol using a differential-type amperometric biosensor based on alcohol dehydrogenase", Analytica Chimica Acta, 390(1-3): p. 83-91, May 1999.*
International Search Report and Written Opinion received in international application No. PCT/EP2019/065994, dated Sep. 20, 2019 (8 pages).
Extended European Search Report received in EP application No. EP18382459.8, dated Dec. 7, 2018 (4 pages).

* cited by examiner

*Primary Examiner* — J. Christopher Ball
(74) *Attorney, Agent, or Firm* — Edell, Shapiro & Finnan, LLC

(57) ABSTRACT

An enzymatic electrochemical method for the quantification of analytes in isolated samples of biological fluids based on a dual biosensor strip electrochemical system. The sample is analyzed in parallel using first and second different biosensor test strips (blank and complete) and the results are obtained by subtracting a response obtained in the electrodes of the first biosensor test strip from a response obtained in the electrodes of the second biosensor test strip, thus eliminating the effect of interferences and isolating the signal corresponding only to the analyte determination.

16 Claims, 3 Drawing Sheets

ENZYMATIC ELECTROCHEMICAL METHOD FOR THE QUANTIFICATION OF ANALYTES IN BIOLOGICAL FLUID SAMPLES

CROSS-REFERENCE TO RELATED APPLICATIONS

This application is a continuation-in-part to International Application No. PCT/EP2019/065994. This application relates to and claims the benefit and priority to International Application No. PCT/EP2019/065994, filed Jun. 18, 2019, which relates to and claims the benefit and priority to European Patent Application No. EP18382459.8, filed Jun. 21, 2018.

FIELD

The present invention refers to an enzymatic electrochemical method to determine and quantify analytes in physiological samples, which is based on the differential measurement of current intensities provided by two biosensor strips containing enzymes and mediators involved in a redox reaction of the analyte to be determined. Therefore, the invention could come under the field of analytical methods.

BACKGROUND

Analyte detection and quantification in physiological samples to directly or indirectly determine a pathology is highly important for today's society, and a great variety of methods and devices therefore exists to detect analytes of interest such as glucose, cholesterol, uric acid, etc. A standard strategy for these detections is to apply electrochemical reactions, particularly reactions where the analyte is an enzyme substrate and where this interaction triggers a flow of electrons that can be directly related to the concentration of the analyte of interest. Documents such as US2016/0177365, US2010/0270175 or EP1770396 describe methods and sensors based on these processes, although these methods are applied to specific analytes in a limited detection range.

However, some of the sensors developed for this purpose end up being large and complex devices whose use is restricted to the laboratory, which means that obtaining the information needed to determine a diagnosis or treatment is a longer process. On the other hand, those sensors are generally used to detect molecules in a high concentration range. Furthermore, there is the additional problem of interferences in such heterogeneous samples as urine or blood, which have numerous components.

Therefore, there is a need for devices that minimise the interferences in the sample matrix and provide accurate determinations even at low analyte concentrations and that are also easy to handle.

SUMMARY

The present invention refers to an enzymatic electrochemical method to determine and quantify analytes in physiological samples which is based on the differential measurement of current intensities measured at ambient temperature between a biosensor strip A (usually referred to as blank) modified with an enzyme and a mediator, and a biosensor strip B (referred to as complete) which contains a cofactor in addition to the enzyme and the mediator and its conversion to analyte concentrations performed using the calibration parameters of the corresponding biosensor strip batch.

The measurement method is based on the amperometric electrochemical technique, where a constant potential is applied during a specific time and the current produced by the electrochemical reaction in the cell at that time is recorded. The conversion from current to analyte concentration occurs by means of a previously established calibration curve, obtained with the measurement device and biosensor strips from the same batch.

The sample is analysed in parallel using two different biosensor strips (blank and complete). The results obtained with both strips are subtracted, thus eliminating any interference effect and isolating the signal corresponding only to the analyte determination.

Each biosensor strip batch is previously calibrated using the corresponding "synthetic biological fluid" sample doped with known concentrations of the analyte to be determined in the range of interest, which are electrochemically measured by amperometry. Calibration codes are thus generated and subsequently used to calculate the analyte concentrations in real samples. The "synthetic biological fluid" is a solution that contains the main interferences of the biological sample and whose electrochemical behaviour is close to the real matrix. Its use together with the dual biosensor strip system enables the determination of low concentrations of analyte in real biological fluids without the need of sample pre-treatment.

In the present invention, a biosensor strip consists of at least three screen-printed electrodes: a reference electrode, which may be Ag/AgCl, Ag, Pt, Au; an auxiliary electrode (or counter electrode), which may be graphite, carbon, Pt, Au; and a working electrode, which may be carbon, graphite, graphene, Au. The screen-printed electrodes are deposited on a substrate, preferably PET, ceramic or paper. Preferably, a layer of isolating ink is screen-printed on top of the electrodes, protecting them from direct contact with the solution and defining the working area. The enzyme, the mediator, the cofactor and other components of the modification, if applicable, are deposited on the working electrode within each test strip. The screen-printed electrodes of strip A and strip B can be deposited on the same piece of substrate and preferably, strip A and strip B share the same reference electrode and the same auxiliary electrode.

According to one embodiment, the applied potential ranges between −0.2 V and +0.2 V vs. Ag/AgCl. The current obtained for each analyte concentration versus the known concentration of that analyte provides the calibration curve for all the biosensor strips produced in the same batch.

In a first aspect, the present invention relates to an enzymatic electrochemical method to quantify analytes in isolated biological fluid samples that comprise the following stages:

a) introduce the sample in an electrochemical system formed by at least a biosensor strip A characterised by comprising at least:
  a working electrode modified with at least one enzyme and one electrochemical mediator,
  a reference electrode and
  an auxiliary electrode or counter-electrode
  and at least a biosensor strip B characterised by comprising at least:
  a working electrode modified with the same enzyme and the same electrochemical mediator as strip A and additionally at least a cofactor,
  a reference electrode and a) an auxiliary electrode or counter-electrode;
b) apply a constant potential during a set period of time;
c) measure the current intensity produced by the reoxidation of the cofactor on the working electrode, facilitated by the mediator, after having been initially reduced due to the reaction between the enzyme and the analyte, on each of the biosensor strips and subtract the response obtained in each of the electrodes of the strip A from the response obtained in each of the corresponding electrodes of the strip B;
d) translate the current intensity data obtained in stage (c) by means of a calibration curve obtained from samples of the synthetic biological fluid comprising different concentrations of the analyte to be determined.

DETAILED DESCRIPTION

Figure 1:
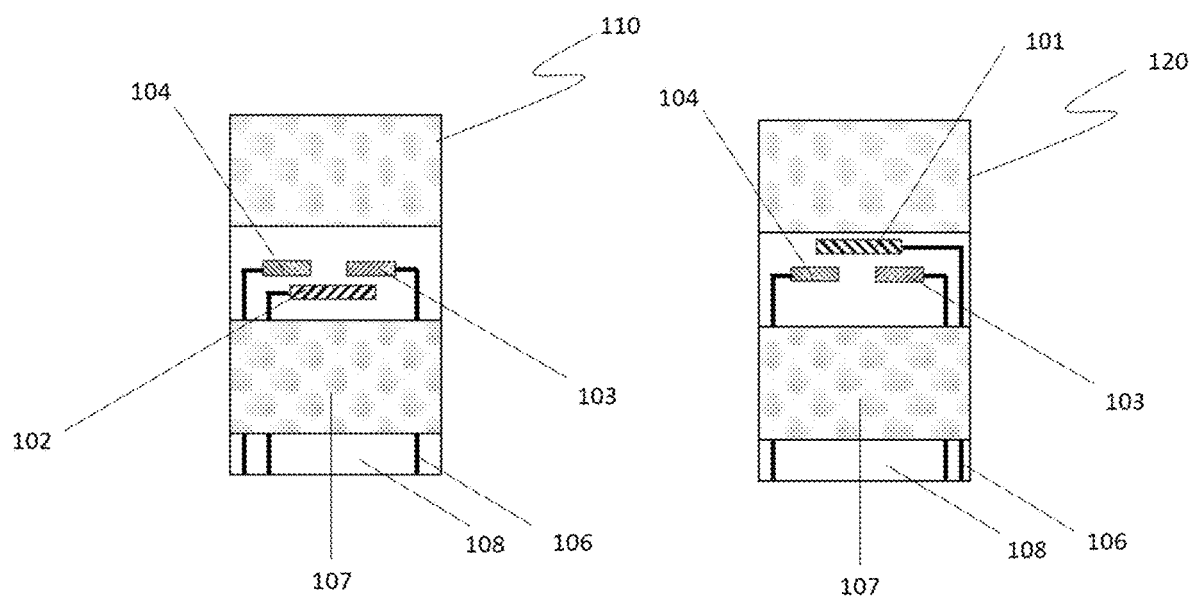
FIG. 1 shows a schematic view of a biosensor strip A and a biosensor strip B according to one embodiment.

FIG. 1 shows one embodiment of biosensor strip A 110 and strip B 120 in different pieces of substrate, where the working electrodes 102, 101, the reference electrode 103 and the auxiliary electrode 104 of each strip are deposited in separated pieces of the substrate 108. Each biosensor strip 110,120 has an insulating layer 107 and electric contacts 106.

Figure 2:
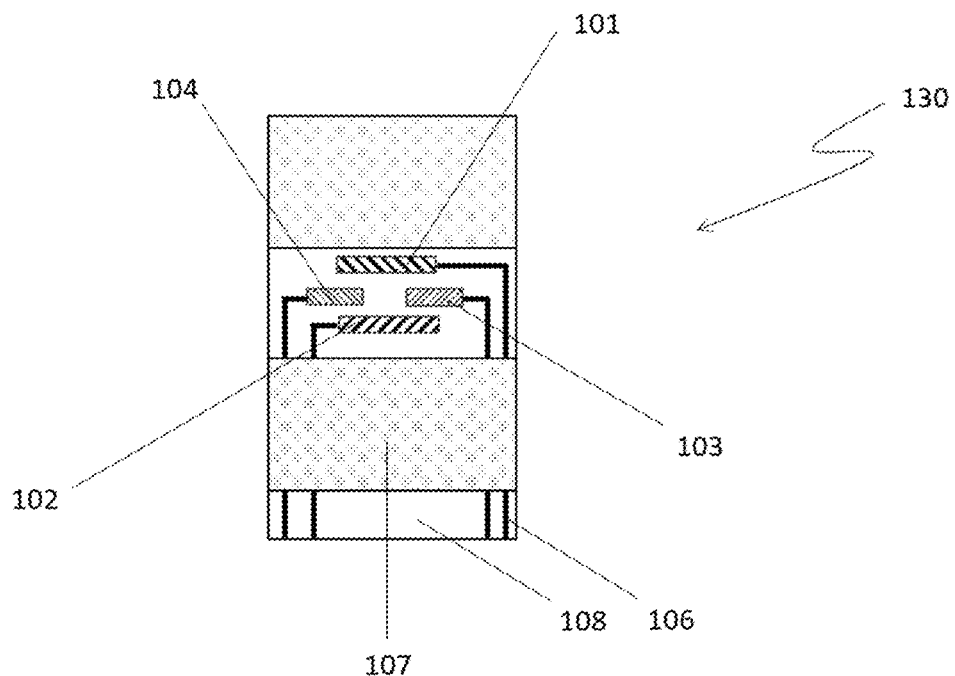
FIG. 2 shows a schematic view of a biosensor strip A and a biosensor strip B according to another embodiment.

FIG. 2 shows another embodiment of the biosensor strip A and B 130, wherein the electrodes of Strip A and Strip B are deposited on the same piece of the substrate 108. Preferably, as shown in FIG. 2, the strip A and strip B share the same reference electrode 103 and the auxiliary electrode 104.

In a preferred embodiment, the enzyme present on the working electrode of the test strips is an oxidoreductase. In a more preferred embodiment, the enzyme is a dehydrogenase, which optionally may be NAD+ or NADP+ dependent. In an even more preferred embodiment, the dehydrogenase enzyme is selected from among lactate dehydrogenase, glucose dehydrogenase, methanol dehydrogenase, glucose-6-phosphate dehydrogenase, malate dehydrogenase, glycerol-3-phosphate dehydrogenase, glycerol dehydrogenase, alcohol dehydrogenase, D-xylose-1-dehydrogenase.

In another preferred embodiment, the mediator present on the working electrode of the biosensor strips is selected from among tetramethylbenzidine (TMB), potassium ferricyanide, toluidine blue, hydroquinone, tetrathiafulvalene (TTF), ferrocene.

In another preferred embodiment, the cofactor present on the working electrode of the biosensor strip B is selected from among NAD+, NADP+, FAD, FMN. Preferably, the cofactor does not form part of the structure of the enzyme.

In another preferred embodiment, the applied potential in stage (b) is between −0.2 V and +0.2V vs. Ag/AgCl. In a more preferred embodiment, the applied potential in stage (b) is between −0.05 V and +0.15 V vs. Ag/AgCl.

In another preferred embodiment, the time during which the potential is applied in stage (b) is between 20 and 120 s. In a more preferred embodiment, the time during which the potential is applied is stage (b) is between 30 and 90 s.

In another preferred embodiment, the fluid sample is an isolated biological sample that is selected from among urine, blood, serum, plasma, pleural fluid or saliva.

To carry out the method of the invention, it is possible using any enzyme that has the analyte to be determined as a substrate, although the enzyme present on the electrodes is preferably an oxidoreductase, more preferably a dehydrogenase, and even more preferably a dehydrogenase which preferably may be dependent on cofactors such as NAD+ or NADP+. The dehydrogenase enzyme is selected from among lactate dehydrogenase, glucose dehydrogenase, methanol dehydrogenase, glucose-6-phosphate dehydrogenase, malate dehydrogenase, glycerol-3-phosphate dehydrogenase, glycerol dehydrogenase, alcohol dehydrogenase, D-xylose-1-dehydrogenase.

In the present invention, a "mediator" is a compound with redox activity that facilitates the electron transfer between the cofactor and the surface of the working electrodes of each test strip, lowering the applied potential (in absolute value) that can be used to determine the analyte. Preferably, the mediator present in the electrodes is selected from among tetramethylbenzidine (TMB), potassium ferricyanide, toluidine blue, hydroquinone, tetrathiafulvalene (TTF), ferrocene.

Preferably, the cofactor is selected from among FAD, FMN, NAD+, NADP+.

Preferably, the cofactor is external and it does not form part of the structure of the enzyme.

The method of the invention is applicable to any biological fluid sample, although preferably, the isolated biological sample is selected from among urine, blood, serum, plasma, pleural fluid or saliva, and more preferably, urine.

The described calibration stage is conducted using analyte solutions in samples of synthetic biological fluids. Typically, an analyte standard prepared in synthetic biological fluid sample is used and it is progressively diluted in the same synthetic sample to obtain the samples for the calibration. Preferably, these concentrations vary depending on the analyte and each measurement is conducted at least in triplicate. A "synthetic biological fluid sample" is understood as an artificial matrix that presents similar characteristics to the natural biological sample (urine, blood, plasma, etc.) and which is obtained by adding the components that it typically comprises of, such as salts, proteins, sugars, etc.

Throughout the description and the claims, the word "comprise" and its variations do not seek to exclude other technical characteristics, additives, components or steps. For the experts in the subject, those items, advantages and characteristics of the invention are partly derived from the description and partly from practicing the invention. The following examples and figures are shown as an illustration of the invention and they do not seek to limit this invention.

EXAMPLES

The invention will be next illustrated by some assays performed by the inventors, showing the effectiveness of the method of the invention.

Example 1: D-Xylose Determination in Different Media

Determination of D-xylose concentration in different matrices, using the biosensor strips previously described and modified to measure D-xylose. In this example, biosensor strips contain D-xylose dehydrogenase as a biological recognition element, NAD+ as an enzyme co-factor and toluidine blue (TBO) as a mediator. The buffer is 200 Mm phosphate buffer pH 8 and the synthetic urine contains 150 mM KCl and 10 giL urea.

Figure 3:
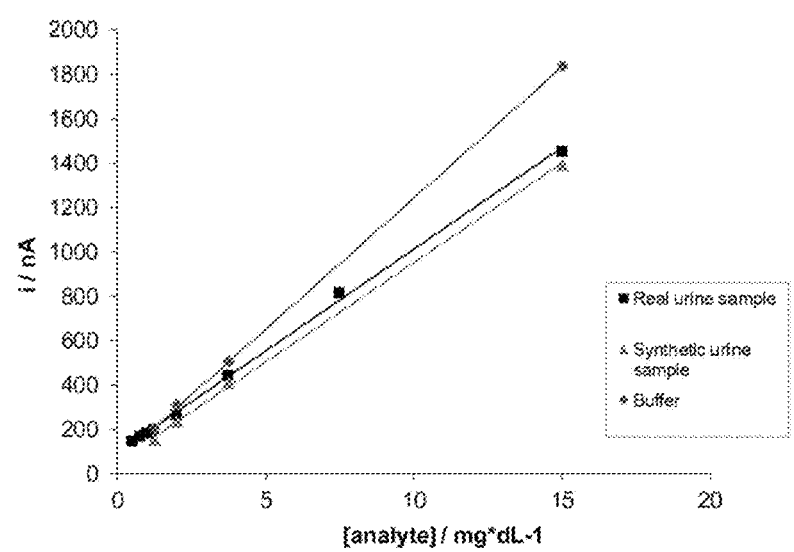
FIG. 3 shows the correlation between the electrical current of D-xylose biosensor strips and D-xylose concentrations in different media.

FIG. 3 shows the electrical current in nanoamperes obtained in buffer, synthetic urine and human urine samples with varying concentrations of D-xylose, when measured at 0V. The results demonstrate that the D-xylose biosensor strip of the present invention has a linear response respect to D-xylose concentration in the range from about 0.75 mg/dL to about 15 mg/dL, in various media. In addition, it can be observed that the calibration curve in buffer was quite different from the calibration curve in human urine samples. However, the calibration curve in synthetic urine is quite similar to the calibration curve in human urine samples, and it can be used for the highly accurate determination of D-xylose in human urine (see FIG. 3).

Figure 4:
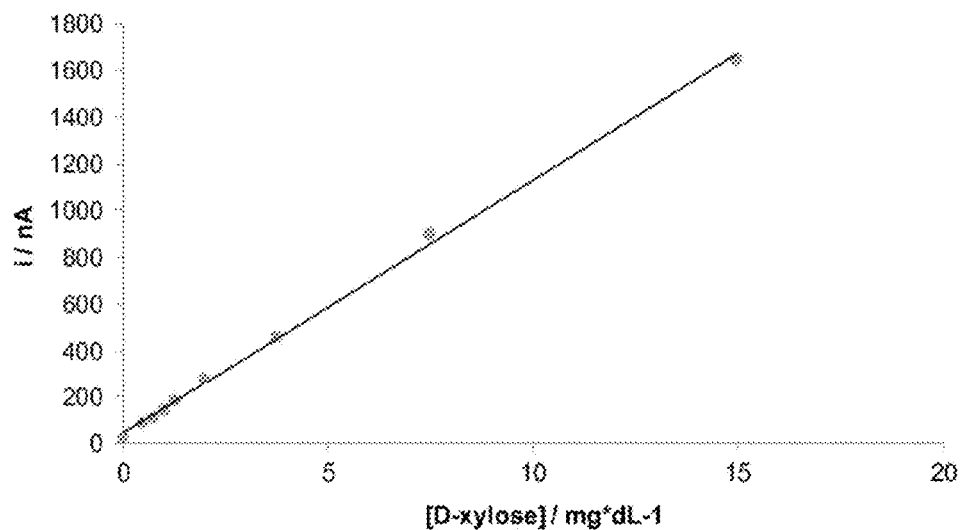
FIG. 4 shows the calibration curve of normalized currents obtained by measuring synthetic urine samples containing varying D-xylose concentrations. Normalized currents are obtained by subtracting the current of a blank biosensor strip from the current shown by a complete biosensor strip.

Example 2: Accuracy of the Method of the Invention for the Determination of D-Xylose Concentration in Human Urine Simples The method consists of two biosensor strips: the blank strip, containing TBO and D-xylose dehydrogenase (XDH) and the complete strip, containing TBO, D-XDH and NAD+. Human urine samples with different D-xylose concentrations were tested using the bi-strip method with the above-described reagent formulations. Currents obtained from both strips were subtracted to separate the matrix effect from the analyte response. D-xylose concentrations in the samples were calculated by means of the calibration curve previously measured in synthetic urine. % error (RSD, n=3) of all measurements were lower than 10% (see FIG. 4).

Table 1 shows the electrical currents in nanoamperes of several human urine samples containing different D-xylose concentrations and the % accuracy respect to the real D-xylose concentration.

| [D-xylose]/ | Urine sample 1 | | Urine sample 2 | | Urine sample 3 | |
| --- | --- | --- | --- | --- | --- | --- |
| mg*dL−1 | i/nA | % recovery | i/nA | % recovery | i/nA | % recovery |
| 0.75 | 134.8 | 112.9 | 119.7 | 94.3 | 121.1 | 96.1 |
| 1.25 | 181.7 | 102.3 | 175.3 | 97.6 | 178.9 | 100.2 |
| 2.0 | 275.8 | 107.3 | 256.0 | 98.2 | 260.0 | 100.0 |
| 3.75 | 449.1 | 99.8 | 431.5 | 95.5 | 415.9 | 91.7 |
| 15 | 1462.0 | 87.2 | 1572.3 | 94.0 | 1403.7 | 83.6 |

Example 3: Comparison of the Accuracy of the Method of the Invention

To compare the method of the invention to other known methods, D-xylose determination in human urine samples was performed using a mono-strip biosensor system and the bi-strip biosensor system of the invention.

Same urine sample containing different D-xylose concentrations was measured using:
1—only one complete biosensor strip of the invention, as above described in example 2,
2—one blank biosensor strip and one complete biosensor strip of the invention, as above described in example 2.

Figure 5:
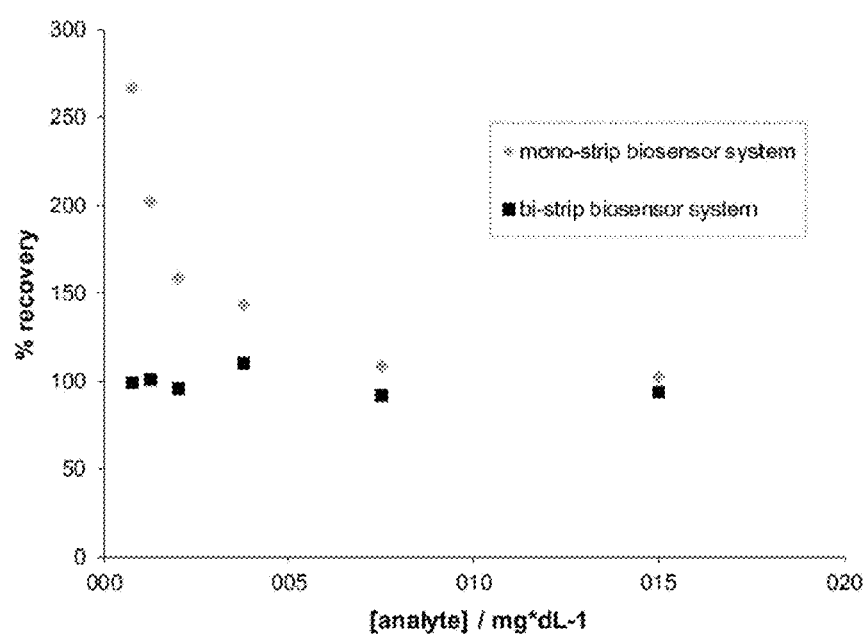
FIG. 5 shows the recovery percentage of D-xylose obtained by measuring real urine samples, expressed as the ratio of calculated concentration to real concentration of D-xylose.

Measurements were performed at 0V and the current obtained was used to calculate the corresponding D-xylose concentration by means of the calibration curve previously obtained in synthetic urine. FIG. 5 shows the recovery percentage of D-xylose expressed as the ratio of concentration levels obtained using the biosensor strips of the invention respect to real concentration levels, by applying only one complete strip or the bi-strip biosensor system above proposed in the invention. As it can be observed, this system improved remarkably the accuracy of the sensor system, especially at low analyte concentrations.

The following clauses represent in a non-limiting way additional embodiments.

Clause 1. Enzymatic electrochemical method for quantification of analytes in isolated biological fluid samples that comprises the following stages:
   a) introduce said sample in an electrochemical system formed by at least a biosensor strip A characterised by comprising at least:
      a working electrode modified with at least an enzyme and an electrochemical mediator,
      a reference electrode and
      an auxiliary electrode or counter-electrode
   and at least a biosensor strip B characterised by comprising at least:
      a working electrode modified with the same enzyme and the same electrochemical mediator as strip A and additionally at least a cofactor,
      a reference electrode and
      an auxiliary electrode or counter-electrode;
   apply a constant potential during a set period of time;
   c) measure the current intensity produced by the re-oxidation of the cofactor on the working electrode, facilitated by the mediator, after having been initially reduced due to the reaction between the enzyme and the analyte, on each of the biosensor strips and subtract the response obtained in each of the electrodes of the strip A from the response obtained in each of the homologous electrode of the strip B;
   d) translate the current intensity data obtained in stage (c) by means of a calibration curve obtained from samples of the synthetic biological fluid comprising different concentrations of the analyte to be determined.

Clause 2. The method according to clause 1, wherein the enzyme present on the working electrode of the test strips is an oxidoreductase.

Clause 3. The method according to clause 2, wherein the enzyme is a dehydrogenase.

Clause 4. The method according to clause 3, where the dehydrogenase enzyme is selected from among lactate dehydrogenase, glucose dehydrogenase, methanol dehydrogenase, glucose-6-phosphate dehydrogenase, malate dehydrogenase, glycerol-3-phosphate dehydrogenase, glycerol dehydrogenase, alcohol dehydrogenase, D-xylose-1-dehydrogenase.

Clause 5. The method according to any one of clauses 1 to 4, wherein the mediator present on the working electrode of the biosensor strips is selected from among tetramethylbenzidine (TMB), potassium ferricyanide, toluidine blue, hydroquinone, tetrathiafulvalene (TTF), ferrocene.

Clause 6. The method according to any one of clauses 1 to 5 wherein the cofactor present on the working electrode of the biosensor strip B is selected from among NAD+, NADP+, FAD, FMN.

Clause 7. The method according to clause 6 wherein the cofactor does not form part of the structure of the enzyme.

Clause 8. The method according to any one of clauses 1 to 7 wherein the potential applied in stage (b) is between −0.2 V and +0.2 V vs. Ag/AgCl.

Clause 9. The method according to clause 8, wherein the potential applied in stage (b) is between −0.05 V and +0.15 V vs. Ag/AgCl.

Clause 10. The method according to any one of clauses 1 to 9, wherein the time during which the potential is applied in stage (b) is between 20 and 120 s.

Clause 11. The method according to clause 10, wherein the time during which the potential is applied in stage (b) is between 30 and 90 s.

Clause 12. The method according to any one of clauses 1 to 11, wherein the fluid sample is an isolated biological sample selected from among urine, blood, serum, plasma, pleural fluid or saliva.

What is claimed is:

1. An enzymatic electrochemical method for quantification of an analyte in a biological fluid sample, the method comprising:
    introducing the biological fluid sample in an electrochemical system formed by a first biosensor strip and a second biosensor strip, the first biosensor strip including a first working electrode modified with an enzyme and an electrochemical mediator, a first reference electrode and a first auxiliary electrode, the second biosensor strip including a second working electrode, a second reference electrode and a second auxiliary electrode, the second working electrode being modified with the enzyme, the electrochemical mediator and a cofactor;
    applying a constant potential to the first and second working electrodes, the first and second reference electrodes and the first and second auxiliary electrodes during a set period of time;
    obtaining current intensity data by measuring a current intensity produced by a re-oxidation of the cofactor on the second working electrode after the cofactor being initially reduced due to a reaction between the enzyme and the analyte on each of the first and second biosensor strips, and subtracting a response obtained in each of the first working electrode, first reference electrode and first auxiliary electrode from a response respectively obtained in each of the second working electrode, second reference electrode and second auxiliary electrode, the re-oxidation of the cofactor being facilitated by the electrochemical mediator;
    translating the current intensity data by use of a calibration curve obtained from samples of a synthetic biological fluid comprising different concentrations of the analyte to be determined.

2. The method according to claim 1, wherein the enzyme present on the first and second working electrodes is an oxidoreductase.

3. The method according to claim 2, wherein the enzyme is a dehydrogenase enzyme.

4. The method according to claim 3, where the dehydrogenase enzyme is selected from the group consisting of lactate dehydrogenase, glucose dehydrogenase, methanol dehydrogenase, glucose-6-phosphate dehydrogenase, malate dehydrogenase, glycerol-3-phosphate dehydrogenase, glycerol dehydrogenase, alcohol dehydrogenase, and D-xylose-1-dehydrogenase.

5. The method according to claim 1, wherein the electrochemical mediator present on each of the first and second working electrodes is selected from the group consisting of tetramethylbenzidine (TMB), potassium ferricyanide, toluidine blue, hydroquinone, tetrathiafulvalene (TTF), and ferrocene.

6. The method according to claim 1, wherein the cofactor present on the second working electrode is selected from the group consisting of nicotinamide adenine dinucleotide (NAD+), nicotinamide adenine dinucleotide phosphate (NADP+), flavin adenine dinucleotide (FAD), and flavin mononucleotide (FMN).

7. The method according to claim 6, wherein the cofactor does not form part of a structure of the enzyme.

8. The method according to claim 1, wherein the potential applied is between −0.2 V and +0.2 V vs. Ag/AgCl.

9. The method according to claim 8, wherein the potential applied is between −0.05 V and +0.15 V vs. Ag/AgCl.

10. The method according to claim 1, wherein the set period of time is between 20 seconds and 120 seconds.

11. The method according to claim 1, wherein the set period of time is between 30 seconds and 90 seconds.

12. The method according to claim 1, wherein the biological fluid sample is an isolated biological sample selected from the group consisting of urine, blood, serum, plasma, pleural fluid and saliva.

13. The method according to claim 1, wherein the first and second biosensor strips reside on a same substrate.

14. The method according to claim 13, wherein the first and second reference electrodes are one and the same.

15. The method according to claim 13, wherein the first and second auxiliary electrodes are one and the same.

16. The method according to claim 14, wherein the first and second auxiliary electrodes are one and the same.

* * * * *